United States Patent [19]

Umezawa et al.

[11] 4,382,926
[45] May 10, 1983

[54] FORMIMIDOYL A AND B USEFUL AS SEMI-SYNTHETIC AMINOGLYCOSIDIC ANTIBIOTICS

[75] Inventors: Hamao Umezawa; Yoshiro Okami, both of Tokyo; Shinichi Kondo, Yokohama, all of Japan

[73] Assignee: Zaidan Hojin Biseibutsu Kagaku Kenkyu Kai, Japan

[21] Appl. No.: 244,232

[22] Filed: Mar. 16, 1981

[30] Foreign Application Priority Data

Apr. 1, 1980 [JP]   Japan ................................. 55-41184
Aug. 6, 1980 [JP]   Japan ................................ 55-107201

[51] Int. Cl.³ ...................... A61K 31/71; C07H 15/22
[52] U.S. Cl. ................................... 424/181; 536/16.1
[58] Field of Search ................. 260/345.9 R, 345.8 R; 424/283, 181; 536/17 B, 17 R

[56] References Cited

U.S. PATENT DOCUMENTS

| | | | |
|---|---|---|---|
| 3,931,400 | 1/1976 | Nara et al. | 260/345.9 R |
| 3,976,768 | 8/1976 | Nara et al. | 424/118 |
| 4,048,015 | 9/1977 | Nara et al. | 260/345.7 R |
| 4,091,032 | 5/1978 | Tadanier et al. | 260/345.7 R |
| 4,097,428 | 6/1978 | Nara et al. | 260/345.9 R |
| 4,145,253 | 3/1979 | Iida et al. | 260/345.9 R |
| 4,173,564 | 11/1979 | Tadanier et al. | 260/345.9 R |
| 4,174,312 | 11/1979 | Tadanier et al. | 260/345.9 R |
| 4,296,106 | 10/1981 | Umezawa et al. | 536/17 B |

OTHER PUBLICATIONS

Yoshida et al., J. Antibiotics, 32, 964 (1979).
Yamamoto et al., ibid, 30, 1064 (1977).
Inouye et al., ibid, 32, 1354 (1979).
Nara et al., ibid, 30, 533 (1977).

*Primary Examiner*—Nicky Chan
*Attorney, Agent, or Firm*—Larson and Taylor

[57] ABSTRACT

New, useful derivatives of istamycins A and B are provided, which are formimidoylistamycins A and B of formula (I) having a toxicity significantly lower than those of istamycins A and B with an antibacterial activity higher than that of fortimicin A and of the same level as those of istamycins A and B. These compounds may be prepared by reacting 1,2′,6′-tri-N-protected istamycins A and B of formula (V) with an iminoether.

5 Claims, No Drawings

FORMIMIDOYL A AND B USEFUL AS SEMI-SYNTHETIC AMINOGLYCOSIDIC ANTIBIOTICS

SUMMARY OF THE INVENTION

This invention relates to new derivatives of istamycins A and B, more particularly formimidoylistamycin A and formimidoylistamycin B and their acid addition salts which are useful as semi-synthetic aminoglycosidic antibiotics and to their preparation.

BACKGROUND OF THE INVENTION

During our investigations on an improvement of useful antibiotics, istamycins A and B, which we already produced by fermentation of a new microorganism, *Streptomyces tenjimariensis* FERM P-4932 (ATCC No. 31603) (Japanese Patent KOKAI No. 145697/80, "Journal of Antibiotics" 32, 964–966 (September 1979); U.K. patent application No. GB 2048855A published Dec. 17, 1980), we noticed an improved antibacterial activity of formimidoylfortimicin A [SF-2052 substance; Journal of Antibiotics, 32, 1354–1356 (1979)] over fortimicin A and tried to apply our finding to istamycins, that is we intended to convert the amino group in the glycine moiety of istamycins A and B to an amidine group, and thus we have now successfully produced new compounds, formimidoylistamycin A and formimidoylistamycin B, which have an antibacterial activity higher than that of fortimicin A and of the same level as those of istamycins A and B and which are of lower toxicity than those of istamycins A and B.

DETAILED DESCRIPTION OF THE INVENTION

According to a first aspect of this invention, there are provided as new compounds formimidoylistamycins A and B of formula (I):

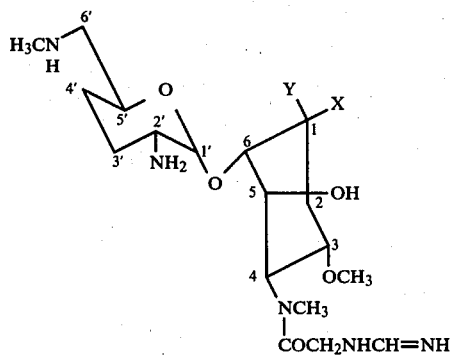

wherein X represents an amino group and Y represents a hydrogen atom for formimidoylistamycin A or X represents a hydrogen atom and Y represents an amino group for formimidoylistamycin B, and their acid addition salts.

Physico-chemical and biological properties of formimidoylistamycins A and B are shown in Tables I and II, respectively.

TABLE I

| Physico-chemical properties | | |
|---|---|---|
| | Formimidoyl-istamycin A .disulfate .trihydrate | Formimidoyl-istamycin B .disulfate .dihydrate |
| Appearance | Colorless powder | Colorless powder |
| Decomposition point | 202–208° C. | 202–210° C. |
| Specific rotation | $[\alpha]_D^{27} + 82°$ (c 1, H$_2$O) | $[\alpha]_D^{23} + 47°$ (c 1, H$_2$O) |
| Elemental analysis (%) | | |
| C | 32.34 (32.42)* | 33.67 (33.33)** |
| H | 6.52 (6.95)* | 6.94 (6.84)** |
| N | 11.82 (12.60)* | 12.35 (12.96)** |
| S | 9.69 (9.62)* | 9.02 (9.87)** |
| Cellulose-thin layer chromatography Rf*** | 0.39 (single spot) | 0.42 (single spot) |

*Calculated values for C$_{18}$H$_{36}$N$_6$O$_5$.2H$_2$SO$_4$.3H$_2$O
**Calculated values for C$_{18}$H$_{36}$N$_6$O$_5$.2H$_2$SO$_4$.2H$_2$O
***Solvent system: propanol-pyridine-acetic acid-water (15:10:3:12 by volume) Color reagent: ninhydrin

TABLE II

| Biological properties (antibacterial spectra) | | |
|---|---|---|
| | Minimum inhibitory concentrations (mcg/ml)*** | |
| Test microorganisms | Formimidoyl-istamycin A* | Formimidoyl-istamycin B** |
| *Staphylococcus aureus* FDA 209P | 1.56 | 0.39 |
| *Staphylococcus aureus* Smith | <0.20 | <0.20 |
| *Staphylococcus aureus* Ap01 | 1.56 | 0.78 |
| *Staphylococcus epidermidis* 109 | 1.56 | 0.78 |
| *Micrococcus flavus* FDA 16 | 0.39 | 0.39 |
| *Sarcina lutea* PCI 1001 | 0.39 | 0.39 |
| *Bacillus anthracis* | 0.39 | <0.20 |
| *Bacillus subtilis* PCI 219 | 0.20 | <0.20 |
| *Bacillus subtilis* NRRL B-558 | 0.39 | <0.20 |
| *Bacillus cereus* ATCC 10702 | 3.13 | 1.56 |
| *Corynebacterium bovis* 1810 | 1.56 | 1.56 |
| *Mycobacterium smegmatis* ATCC 607 | 0.78 | 0.39 |
| *Escherichia coli* NIHJ | 3.13 | 3.13 |
| *Escherichia coli* K-12 | 3.13 | 1.56 |
| *Escherichia coli* K-12 R5 | 6.25 | 3.13 |
| *Escherichia coli* K-12 R388 | 1.56 | 1.56 |
| *Escherichia coli* K-12 J5R11-2 | 3.13 | 1.56 |
| *Escherichia coli* K-12 ML1629 | 6.25 | 1.56 |
| *Escherichia coli* K-12 ML1630 | 6.25 | 1.56 |
| *Escherichia coli* K-12 ML1410 | 6.25 | 1.56 |
| *Escherichia coli* K-12 ML1410 R81 | 3.13 | 1.56 |
| *Escherichia coli* K-12 LA290 R55 | 6.25 | 1.56 |
| *Escherichia coli* K-12 LA290 R56 | 3.13 | 1.56 |
| *Escherichia coli* K-12 LA290 R64 | 3.13 | 1.56 |
| *Escherichia coli* W677 | 3.13 | 1.56 |
| *Escherichia coli* JR66/W677 | 6.25 | 1.56 |
| *Escherichia coli* K-12 C600 R135 | 100 | 50 |
| *Escherichia coli* JR225 | 3.13 | 1.56 |
| *Klebsiella pneumoniae* PCI602 | 3.13 | 1.56 |
| *Klebsiella pneumoniae* 22#3038 | 6.25 | 3.13 |
| *Shigella dysenteriae* JS11910 | 12.5 | 3.13 |
| *Shigella flexneri* 4B JS11811 | 6.25 | 3.13 |
| *Shigella sonnei* JS11756 | 12.5 | — |
| *Salmonella typhi* T-63 | 1.56 | 0.78 |
| *Salmonella enteritidis* 1891 | 3.13 | 1.56 |
| *Proteus vulgaris* OX19 | 1.56 | 0.78 |
| *Proteus rettgeri* GN311 | 25 | 12.5 |
| *Proteus rettgeri* GN466 | 6.25 | 6.25 |
| *Serratia marcescens* | 12.5 | 6.25 |
| *Serratia* sp. SOU | >100 | >100 |
| *Serratia* sp. 4 | 100 | 100 |
| *Providencia* sp. Pv16 | 12.5 | 12.5 |
| *Providencia* sp. 2991 | 12.5 | 6.25 |
| *Pseudomonas aeruginosa* A3 | 6.25 | 12.5 |
| *Pseudomonas aeruginosa* No.12 | 100 | 100 |
| *Pseudomonas aeruginosa* H9 | 50 | 100 |
| *Pseudomonas aeruginosa* H11 | 100 | >100 |
| *Pseudomonas aeruginosa* TI-13 | 50 | 100 |
| *Pseudomonas aeruginosa* GN315 | 25 | 50 |

TABLE II-continued

| | Biological properties (antibacterial spectra) | |
|---|---|---|
| | Minimum inhibitory concentrations (mcg/ml)*** | |
| Test microorganisms | Formimidoyl-istamycin A* | Formimidoyl-istamycin B** |
| *Pseudomonas aeruginosa* 99 | >100 | >100 |
| *Pseudomonas aeruginosa* B-13 | >100 | >100 |
| *Pseudomonas aeruginosa* 21-75 | >100 | >100 |
| *Pseudomonas aeruginosa* PST1 | >100 | >100 |
| *Pseudomonas aeruginosa* ROS 134/PU21 | >100 | >100 |
| *Pseudomonas aeruginosa* K-Ps 102 | 50 | 100 |
| *Pesudomonas maltophilia* GN907 | >100 | >100 |

*In the form of disulfate.trihydrate
**In the form of disulfate.dihydrate
***Determined according to a standard serial dilution method on nutrient agar plates as incubated at 37° C. for 17 hours.

Formimidoylistamycins A and B are characterized by their low toxicity. Thus, a determination of acute toxicity of these compounds and istamycin B on mice by intravenous administration showed that at a dose of 300 mg/kg of formimidoylistamycin A.disulfate.trihydrate or formimidoylistamycin B.disulfate.dihydrate, all the mice tested survived, whereas at a dose of 150 mg/kg of istamycin B, all the mice tested died.

Formimidoylistamycins A and B of this invention may usually be obtained in the form of the free base, a hydrate or a carbonate thereof and they can be converted, more preferably in view of their stability, into a pharmaceutically non-toxic acid addition salt by adding a pharmaceutically acceptable acid in a usual manner. Examples of pharmaceutically acceptable acids are inorganic acids such as hydrochloric, hydrobromic, sulfuric, phosphoric and nitric acids and organic acids such as acetic, malic, citric, ascorbic and methanesulfonic acids.

According to a second aspect of this invention, there is provided a process for the preparation of formimidoylistamycin A or B of formula (I):

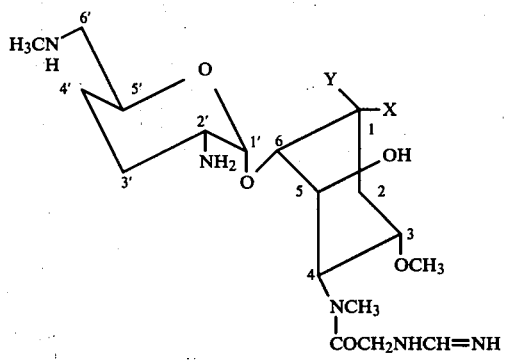

(I)

wherein X represents an amino group and Y represents a hydrogen atom for formimidoylistamycin A or X represents a hydrogen atom and Y represents an amino group for formimidoylistamycin B or an acid addition salt thereof which comprises reacting a compound of formula (V):

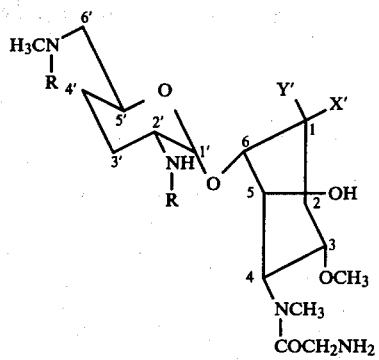

(V)

wherein X' represents an —NHR group and Y' represents a hydrogen atom for istamycin A series or X' represents a hydrogen atom and Y' represents an —NHR group for istamycin B series and R represents a monovalent amino-protecting group, with an iminoether to convert the amino group in the glycine moiety of the compound of formula (V) into an amidine group, thus forming a compound of formula (VI):

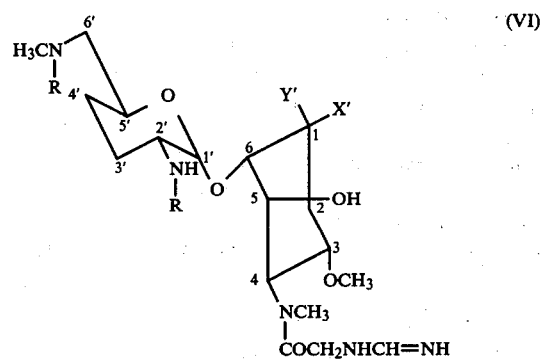

(VI)

wherein X', Y' and R have the same meanings as defined above and removing the amino-protecting groups in the 1-, 2' and 6'-positions in a known manner.

The compounds of formula (V) to be used as starting material of the process according to the second aspect of this invention correspond to 1,2',6'-tri-N-protected derivative of istamycins A and B and may be derived from istamycins A₀ and B₀ (see Japanese Patent Application No. 117912/79; U.K. patent application No. GB 2048855A; U.S. patent application Ser. No. 141,492), respectively, of formula (II):

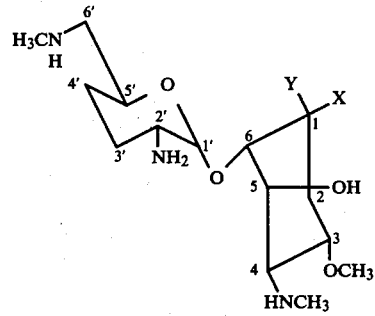

(II)

wherein X represents an amino group and Y represents a hydrogen atom for istamycin A₀ or X represents a hydrogen atom and Y represents an amino group for istamycin $B_0$. Thus, the compounds of formula (V) are prepared by protecting simultaneously the amino and methylamino groups in the 1-, 2'- and 6'-positions of istamycin $A_0$ or $B_0$ with a known amino-protecting group to form a compound of formula (III)

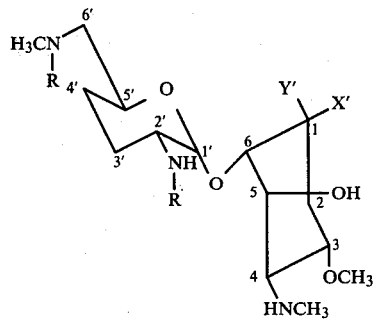

wherein X' represents an —NHR group and Y' represents a hydrogen atom for istamycin A series or X' represents a hydrogen atom and Y' represents an —NHR group for istamycin B series and R represents a monovalent amino-protecting group, reacting the compound of formula (III) with an N-protected glycine whose amino-protecting group is one different from those on the 1-, 2'- and 6'-positions or a reactive derivative thereof to acylate the 4-methylamino group, thus forming a compound of formula (IV):

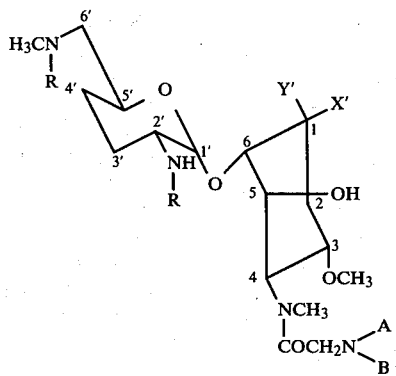

wherein X', Y' and R have the same meanings as defined above, A represents a hydrogen atom and B represents a monovalent amino-protecting group or A and B together form a divalent amino-protecting group and then selectively removing the amino-protecting group on the amino group in the glycine moiety to give the compound of formula (V) above which corresponds to a compound of formula (IV) provided that both A and B represent a hydrogen atom.

PREFERRED EMBODIMENTS OF THE INVENTION

Preferred embodiments for the preparation of the starting compound of formula (V) are given below.

Istamycin $A_0$ or $B_0$ of formula II above is used as starting material for this purpose. In the first step, the 1- and 2'-amino groups and 6'-methylamino group are simultaneously protected with a monovalent amino-protecting group without affecting the 4-methylamino group. As such a monovalent amino-protecting group usually used, there may be exemplified an alkoxycarbonyl group, particularly having 2–7 carbon atoms, such as tert-butoxycarbonyl and tert-amyloxycarbonyl; a cycloalkyloxycarbonyl group, particularly having 4–7 carbon atoms such as cyclohexyloxycarbonyl; an aralkyloxycarbonyl group such as benzyloxycarbonyl; and an acyl group, particularly an alkanoyl group having 2–7 carbon atoms such as trifluoroacetyl and o-nitrophenoxyacetyl. The introduction of such an amino-protecting group may be carried out in a manner known in the syntheses of peptides, e.g. by using a known amino-protecting group-introducing reagent in the form of an acid halide, an acid azide, an active ester, an acid anhydride, etc. By using such an amino-protecting group-introducing reagent in an amount of 2.5–3.5 moles per mole of istamycin $A_0$ or $B_0$, it is possible to preferentially form 1,2',6'-tri-N-protected istamycin $A_0$ or $B_0$ of formula (III) above due to the difference in reactivity of respective amino and methylamino groups of istamycin $A_0$ or $B_0$. Alternatively, 1,2',6'-tri-N-protected istamycin $A_0$ or $B_0$ of formula (III) may be obtained in a higher yield by reacting istamycin $A_0$ or $B_0$ with one molar equivalent of a divalent cation such as those of divalent transition metals such as copper, nickel and cobalt and of zinc (II) to form a metal complex and reacting the complex with 3–5 moles of an amino-protecting group-introducing reagent, followed by removal of the metal cation from the reaction product.

The subsequent glycylation (i.e. acylation with glycine) of the 4-methylamino group of the 1,2',6'-tri-N-protected istamycin $A_0$ or $B_0$ of formula (III) may be effected by reacting the compound with glycine or a reactive derivative thereof in accordance with any of known N-acylation processes for peptide-syntheses such as the dicyclohexylcarbodiimide process, mixed acid anhydride process, azide process, active ester process, etc. It is preferable for the glycine reagent to have the amino group protected, and the amino-protecting group for this purpose must be one which is different from those on the 1- and 2'-amino groups and on the 6'-methylamino group of istamycin $A_0$ or $B_0$ and which is easily removable. Thus, the amino-protecting group for protecting the amino group in the glycine reagent may be selected from the above-mentioned amino-protecting groups and some divalent amino-protecting groups such as ones of a Schiff base type. The acylation reaction with a glycine reagent is preferably carried out according to an active ester process in an organic solvent such as dioxane under heating to a temperature of 40°–60° C., thus giving a compound of formula (IV) above. In one preferred example, 1,2',6'-tri-N-benzyloxycarbonylistamycin $A_0$ is acylated on the 4-methylamino group with N-hydroxysuccinimide ester of N-tert-butoxycarbonylglycine, thus forming a N-protected intermediate compound of formula (IV) wherein R is benzyloxycarbonyl group, A is hydrogen and B is tert-butoxycarbonyl group. According to another preferred embodiment, 1,2',6'-tri-N-tert-butoxycarbonylistamycin $B_0$ is acylated on the 4-methylamino group with N-hydroxysuccinimide ester of N-benzyloxycarbonylglycine, thus forming an N-protected intermediate compound of formula (IV) in which R is tert-butoxycarbonyl, A is hydrogen and B is benzyloxycarbonyl group.

The next step is for the selective removal of the amino group in the glycine moiety of the amino- and methylamino-protected compound of formula (IV) to obtain the desired starting compound of formula (V) above which corresponds to 1,2',6'-tri-N-protected istamycin A or B. The removal of the amino-protecting group on the amino group in the glycine moiety of the compound of formula (IV) may usually be effected in a known manner, for example, by hydrogenolysis in the presence of palladium, platinum oxide, etc. as catalyst for the removal of an aralkyloxy-carbonyl group or by hydrolysis in an aqueous solution of trifluoroacetic acid, acetic acid, etc. or a diluted aqueous acid solution such as a diluted hydrochloric acid for the removal of other amino-protecting groups.

Typical embodiments for carrying out the process of this invention is now explained. In the first step of this process, the compound of formula (V) is reacted with an iminoether to convert the amino group in the glycine moiety of 1,2',6'-tri-N-protected istamycin A or B into an amidine group. The iminoether reagent may be one having the general formula:

R'OCH=NH wherein R' represents a lower alkyl group or an aralkyl group such as benzyl or an acid addition salt thereof such as hydrochloride and sulfate. The use of an iminoether hydrochloride such as ethylformimidate hydrochloride and benzylformimidate hydrochloride is preferred. The reaction may be conducted in an organic solvent such as dioxane and methanol or in an aqueous solution at a temperature of below 30° C. in a known manner. The resulting compound of formula (VI), 1,2',6'-tri-N-protected formimidoylistamycin A or B, or an acid addition salt thereof may be purified by a column chromatography using a silica gel and the like. In the second step of the process according to this invention, the remaining amino-protecting groups on the compound of formula (VI) may be removed by a known method as above-mentioned, thus to yield the desired formimidoylistamycin A or B of formula (I) in the form of an acid addition salt.

Thus, by combining the process of this invention with the process for the preparation of the starting compound of formula (V) as above-mentioned, there is established a process for the preparation of formimidoylistamycin A or B from istamycin $A_0$ or $B_0$ which summarily comprises acylating the 4-methylamino group of istamycin $A_0$ or $B_0$ with formimidoylglycine. The overall process for this purpose comprises the steps of protecting the 1- and 2'-amino groups and 6'-methylamino group of istamycin $A_0$ or $B_0$, with an amino-protecting group, introducing a glycyl group on the 4-methylamino group of the 1,2',6'-tri-N-protected istamycin $A_0$ or $B_0$, converting the glycyl group into a formimidoglycyl group and then deprotecting all the protected amino and methylamino groups of the resulting compound.

The formimidoylistamycins A and B of this invention have a high antibacterial activity and are of a low toxicity to animals. Accordingly, formimidoylistamycins A and B are useful similarly to the antibiotics known as the antibacterial agent and may be formulated into known pharmaceutical forms and administered in the same manner as the known antibacterial antibiotic agents. According to a further aspect of this invention, therefore, there is provided a pharmaceutical composition comprising a safe and effective antibacterial amount of at least one of formimidoylistamycin A, formimidoylistamycin B and acid-addition salt thereof, in combination with a pharmaceutically acceptable carrier. According to another aspect of this invention, there is provided a method for inhibiting bacterial growth which comprises administering an antibacterially effective amount of at least one of formimidoylistamycin A, formimidoylistamycin B and acid-addition salts thereof to an animal susceptible to the bacterial growth. It will be appreciated that the actual preferred amounts of the formimidoylistamycin A or B used will vary according to the particular composition formulated, the mode of application and the particular situs and organism being treated. Many factors which modify the action of the drug will be taken into account by the skilled in the art, for example, age, body weight, sex, diet, time of administration, rate of excretion, drug combinations, reaction sensitivities and severity of the disease. Optimal application rates for a given set of conditions can be ascertained by the skilled in the art using conventional dosage determination tests in view of the above guide-lines. By way of general guideline, suitable dosages of formimidoylistamycins A and B by intramuscular injection for the effective treatment of bacterial infections are in a range of 50 to 500 mg per person two to four times per day.

The following Examples further illustrate the preparation of the compounds according to this invention covering the overall steps starting from istamycin $A_0$ or $B_0$.

EXAMPLE 1

Preparation of formimidoylistamycin A (1) 1,2',6'-Tri-N-benzyloxycarbonylistamycin $A_0$ (formula (III) where R=benzyloxycarbonyl, X'=—NHR, Y'=hydrogen)

To a solution of istamycin $A_0$ (1.0 g, 3.0 mmol) in methanol (40 ml) was added triethylamine (0.72 ml) and then a solution of N-benzyloxycarbonyloxysuccinimide (2.1 g, 8.1 mmol) in methanol (12 ml) under stirring and the resulting mixture was stirred at room temperature for 2 hours. The reaction solution was then concentrated to dryness and the residue was dissolved in chloroform (60 ml). The chloroform solution was washed with water (60 ml) and the chloroform layer was concentrated to dryness to yield a crude powder (2.17 g). The powder was dissolved in dichloromethane (3 ml) and the solution was passed through a column of 55 g of silica gel (CC-7, a product of Mallinckrodt Inc.). The column was then washed with a mixture (560 ml) of dichloromethane-ethanol (150:1 by volume) and eluted with a mixture of the same solvents (20:1 by volume) to yield the titled compound in the form of powder (931 mg). Yield 42%.

(2) 1,2',6'-Tri-N-benzyloxycarbonyl-2"-N-tert-butoxycarbonylistamycin A (formula (IV) where R=benzyloxycarbonyl, A=hydrogen, B=tert-butoxycarbonyl, X'=—NHR, Y'=hydrogen)

1,2',6'-Tri-N-benzyloxycarbonylistamycin $A_0$ (931 mg, 1.27 mmol) obtained in the step (1) above was dissolved in dioxane (30 ml), to which was then added a solution of triethylamine (0.42 ml) and N-hydroxysuccinimide ester of N-tert-butoxycarbonylglycine (830 mg, 3.0 mmol) in dioxane (5 ml) and the mixture was stirred at 60° C. for 4.5 hours. The reaction solution was concentrated to dryness to give a crude powder. The powder was dissolved in dichloromethane (5 ml) and the solution was passed through a column of 150 g of silica gel (CC-7, a product of Mallinckrodt Inc.). The column was then eluted with a mixture of dichloromethane-ethanol (200:1 by volume). The resulting crude powder was dissolved in methanol (5 ml) and the solution was passed through a column of 100 ml of Sephadex LH-20 (a product of Pharmacia Co., Sweden). The column was eluted with methanol to afford the titled compound in a pure powder form (438 mg). Yield 39%.

(3) Formimidoylistamycin A (formula (I) where X=amino, Y=hydrogen)

1,2',6'-Tri-N-benzyloxycarbonyl-2''-N-tert-butoxycarbonylistamycin A (388 mg, 0.44 mmol) obtained in the step (2) above was dissolved in 90% aqueous trifluoroacetic acid solution (5 ml) and the solution was allowed to stand at room temperature for 45 minutes and then concentrated to dryness. The residue was washed with ethyl ether (20 ml) to give 1,2',6'-tri-N-benzyloxycarbonylistamycin A trifluoroacetate (375 mg). The trifluoroacetate was dissolved in a mixture of methanol (60 ml) and water (8 ml), to which was then added dropwise a solution of benzylformimidate hydrochloride (426 mg, 2.5 mmol) in methanol (10 ml) over about 15 minutes under ice-cooling while the pH of the solution was adjusted to 8.5 with the addition of 0.5 N aqueous potassium hydroxide solution. The reaction mixture was stirred for further one hour under ice-cooling for the completion of the introduction of formimidoyl group —CH=NH, then adjusted the pH to 3.7 with the addition of 1 N hydrochloric acid and concentrated to dryness. The residue was dissolved in chloroform (100 ml) and washed with water (30 ml×2) and the chloroform layer separated was concentrated to dryness to yield a crude powder (411 mg). The powder was dissolved in a mixture (3 ml) of chloroform-methanol (20:1 by volume) and the solution was chromatographically purified by passing it through a column of 20 g of silica gel (CC-7) followed by eluting with a mixture of chloroform-methanol (20:1 by volume). Thus, there was obtained 1,2'6'-tri-N-benzyloxycarbonyl-2''-N-formimidoylistamycin A hydrochloride (193 mg) as a powder. Yield 54%.

The powder thus obtained (193 mg, 0.24 mmol) was dissolved in a mixture (12 ml) of methanol-acetic acid-water (2:1:1 by volume), to which 5% palladium-carbon (100 mg) was added and the mixture was subjected to hydrogenolysis in a hydrogen stream at room temperature for 4 hours to remove the remaining amino-protecting groups. After the removal of the catalyst by filtration, the reaction solution was concentrated to dryness and the residue was dissolved in water (1 ml). The solution was passed through a column of 12 ml of a strongly basic anion exchange resin, Amberlite IRA 400 ($SO_4$ form; a product of Rohm & Haas Co.). The elution with water followed by concentration of the eluate to dryness afforded the titled compound in the form of disulfate.trihydrate as a powder (134 mg). Yield 82%.

EXAMPLE 2

Preparation of formimidoylistamycin B (1) 1,2',6'-Tri-N-tert-butoxycarbonylistamycin $B_0$ (formula (III) where R=tert-butoxycarbonyl, X'=hydrogen, Y'=—NHR)

To a solution of istamycin $B_0$ (500 mg, 1.5 mmol) in methanol (20 ml), zinc acetate (500 mg, 2.3 mmol) was added and the mixture was stirred at room temperature for 5 hours. Then, there was added to the mixture 2-(tert-butoxycarbonyloxyimino)-2-phenylacetonitrile (17.1 g, 6.9 mmol; a product of Aldorich Co., U.S.A. under the name of BOC-ON) and the mixture was stirred overnight at room temperature. The reaction solution was concentrated to dryness and the powder was purified by a silica gel-column chromatography (silica gel: 100 g of Wako gel C-200, a product of Wako Junyaku K.K.; eluent: chloroform-methanol=10:1 by volume), affording the titled compound as a powder (412 mg). Yield 44%. Decomposition point 71°-74° C.; $[\alpha]_D^{22}+50°$ (c 1.0, methanol); Rf 0.28 in silica gel TLC (chloroform-methanol=4:1 by volume).

(2) 2''-N-Benzyloxycarbonyl-1,2',6'-tri-N-tert-butoxycarbonylistamycin B (formula (IV) where R=tert-butoxycarbonyl, A=hydrogen, B=benzyloxycarbonyl, X'=hydrogen, Y'=—NHR)

1,2',6'-Tri-N-tert-butoxycarbonylistamycin $B_0$ (200 mg, 0.32 mmol) obtained in the step (1) above was dissolved in dioxane (6 ml) and to the solution were added triethylamine (0.10 ml) and N-hydroxysuccinimide ester of N-benzyloxycarbonylglycine (235 mg, 0.76 mmol). The mixture was stirred at 60° C. for 2 hours followed by concentration to dryness to give a crude powder. The powder was purified by a silica gel-column chromatography (silica gel: 30 g of Wako gel C-200; eluent: ethyl acetate-toluene=3:2 by volume) to obtain a purified powder which was further purified by dissolving it into methanol and passing the solution through a column of 30 ml of Sephadex LH-20 (a product of Pharmacia Co., Sweden) to yield, after the concentration to dryness, a powder of the titled compound (246 mg). Yield 94%. Decomposition point 104°-110° C.; $[\alpha]_D^{23}+44°$ (c 1, methanol); Rf 0.45 in silica gel TLC (ethyl acetate-toluene=7:2 by volume).

(3) 1,2',6'-Tri-N-tert-butoxycarbonylistamycin B (formula (V) where R=tert-butoxycarbonyl, X'=hydrogen, Y'=—NHR)

2''-N-Benzyloxycarbonyl-1,2',6'-tri-N-tert-butoxycarbonylistamycin B (237 mg, 0.29 mmol) obtained in the step (2) above was dissolved in 80% methanol (15 ml) and acetic acid (0.01 ml). The solution was subjected to hydrogenolysis in a hydrogen stream in the presence of 5% palladium-carbon (50 mg) at room temperature and under atmospheric pressure to remove the benzyloxycarbonyl group. Subsequent concentration of the solution to dryness gave a crude powder of the titled compound (237 mg) in the form of acetate.

(4) Formimidoylistamycin B (formula (I))

The crude powder of 1,2',6'-tri-N-tert-butoxycarbonylistamycin B acetate (200 mg) obtained in the step (3) above was dissolved in methanol (20 ml) and ethylformimidate hydrochloride (233 mg, 2.1 mmol) was added to the solution. The mixture was stirred at room temperature for 4 hours to introduce a formimidoyl group —CH=NH. The reaction solution was concentrated to dryness and the resulting powder was purified by a silica gel-column chromatography (silica gel: 42 g of Wako gel C-200; eluent: chloroform-methanol=7:1 by volume), affording 1,2',6'-tri-N-tert-butoxycarbonyl-formimidoylistamycin B hydrochloride as a powder (82 g). Yield 38%.

This powder (54 g, 0.071 mmol) was dissolved in 90% trifluoroacetic acid (2 ml) and the solution was maintained at 0°-5° C. for 2 hours to proceed the deprotection reaction and then concentrated to dryness. The crude powder thus obtained was dissolved in water and the solution was passed through a column of 4 ml of a strongly basic anion exchange resin, Amberlite IRA 400 ($SO_4$ form; a product of Rohm & Haas Co.). The elution with water followed by concentration of the eluate to dryness gave the titled compound in the form of disulfate.dihydrate as a power (45 mg). Yield 97%.

What we claim is:

1. Formimidoylistamycins A and B of formula (I):

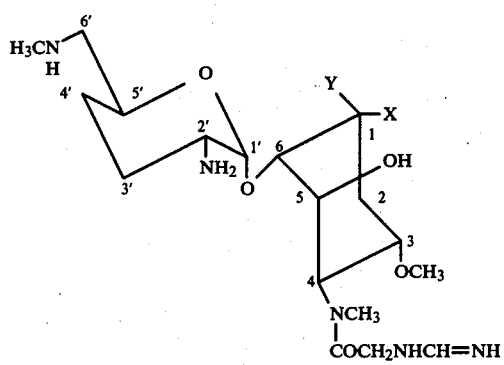

wherein X represents an amino group and Y represents a hydrogen atom for formimidoylistamycin A or X represents a hydrogen atom and Y represents an amino group for formimidoylistamycin B, and their acid addition salts.

2. Formimidoylistamycin A and an acid addition salt thereof.

3. Formimidoylistamycin B and an acid addition salt thereof.

4. A pharmaceutical composition comprising a safe and effective antibacterial amount of at least one of formimidoylistamycin A, formimidoylistamycin B and pharmaceutically acceptable acid-addition salts thereof, in combination with a pharmaceutically acceptable carrier.

5. A method for inhibiting the bacterial growth which comprises administering an antibacterially effective amount of at least one of formimidoylistamycin A, formimidoylistamycin B and pharmaceutically acceptable acid-addition salts thereof to an animal susceptible to the bacterial growth.

* * * * *